(12) United States Patent
Huang et al.

(10) Patent No.: US 12,127,827 B2
(45) Date of Patent: Oct. 29, 2024

(54) ESTIMATION DEVICE, ESTIMATION METHOD, AND PROGRAM (71) Applicant: NEC Corporation, Tokyo (JP)

(72) Inventors: Chenhui Huang, Tokyo (JP); Kenichiro Fukushi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 334 days.

(21) Appl. No.: 17/635,510

(22) PCT Filed: Aug. 28, 2019

(86) PCT No.: PCT/JP2019/033689
§ 371 (c)(1),
(2) Date: Feb. 15, 2022

(87) PCT Pub. No.: WO2021/038748
PCT Pub. Date: Mar. 4, 2021

(65) Prior Publication Data
US 2022/0273193 A1 Sep. 1, 2022

(51) Int. Cl.
A61B 5/11 (2006.01)
A61B 5/00 (2006.01)
A61B 5/16 (2006.01)
G01P 13/00 (2006.01)

(52) U.S. Cl.
CPC ............ *A61B 5/112* (2013.01); *A61B 5/1121* (2013.01); *A61B 5/165* (2013.01); *A61B 5/7278* (2013.01); *G01P 13/00* (2013.01)

(58) Field of Classification Search
CPC ....... G01P 13/00; A61B 5/7278; A61B 5/165; A61B 5/1121; A61B 5/112
See application file for complete search history.

(56) References Cited

U.S. PATENT DOCUMENTS 5,955,667 A 9/1999 Fyfe
2013/0123669 A1 5/2013 Kinoshita et al.

FOREIGN PATENT DOCUMENTS

| JP | 2012-024449 A | 2/2012 |
| JP | 5724237 B | 5/2015 |
| JP | 2016-147069 A | 8/2016 |

OTHER PUBLICATIONS

Kazuki et al., "A Study on Normal walking in Elderly People with Special Reference to Foot Angle and Step Width, Mar. 2011, Osaka Research Journal of Physical Research, vol. 49, pp. 1-13" (Year: 2011).*
JP Office Action for JP Application No. 2021-541865, mailed on Jan. 17, 2023 with English Translation.
International Search Report for PCT Application No. PCT/JP2019/033689, mailed on Nov. 19, 2019.
Kazuki Miyatsuji et al., "A study on normal walking in elderly people with special reference to foot angle and step width", Osaka Research Journal of PhysicalEducation, vol. 49, pp. 1-13, 2018.

(Continued)

*Primary Examiner* — Jamel E Williams (57) ABSTRACT

An estimation device calculates an angle formed by a tip direction of a left foot and a tip direction of a right foot. The estimation device estimates a stride width indicating an interval between heels of the left foot and the right foot, based on the angle.

7 Claims, 12 Drawing Sheets (56) References Cited

OTHER PUBLICATIONS

Yangjian Huang et al., "Novel Foot Progression Angle Algorithm Estimation via Foot-Worn", Magneto-Inertial Sensing, IEEE Transactions on Biomedicalengineering, vol. 63, No. 11, Nov. 2018, pp. 2278-2285.

Haisheng Xia et al., "Validation of a smart shoe for estimating foot progression angle during walking gait", Journal of Biomechanics, 61, 2017, pp. 193-198.

* cited by examiner

ESTIMATION DEVICE, ESTIMATION METHOD, AND PROGRAM

This application is a National Stage Entry of PCT/JP2019/033689 filed on Aug. 28, 2019, the contents of all of which are incorporated herein by reference, in their entirety.

TECHNICAL FIELD

The present invention relates to an estimation device, an estimation method and a program.

BACKGROUND ART

Stride width that indicates the distance between the heels of the left foot and right foot during walking is associated with muscle strength of the lower limbs, walking stability, and an increase in joint load, such that it is known that the larger the stride width, the weaker the muscle strength of the lower limbs, the lower the walking stability, and the greater the possibility of increased joint burden. When the state of a large stride width continues, the fatigue of a person will increase.

Patent Document 1 is disclosed as a related technique. In the technique of Patent Document 1, a gait change determination device is attached to the lumbar region, and based on the acceleration detected by the gait change determination device, the trajectory during walking is specified, and from that trajectory is calculated the stride width, which is one of the indices indicating walking posture (Patent Document 1, paragraph 0124 etc.).

PRIOR ART DOCUMENTS

Patent Documents

Patent Document 1: Japanese Patent No. 5724237

SUMMARY OF THE INVENTION

Problem to be Solved by the Invention

In order to detect fatigue in walking as described above, a technique for estimating stride width with higher accuracy is required. In the technique of Patent Document 1, the trajectory of walking cannot be obtained accurately due to the influence of the movements of the knees and hip joints. As a result, there is a possibility that better calculation accuracy of the stride width cannot be obtained.

Means for Solving the Problem

Therefore, an object of the present invention is to provide an estimation device, an estimation method, and a program that solve the above-mentioned problem.

Effect of Invention

According to a first example aspect of this example embodiment, an estimation device includes: an angle calculation unit that calculates an angle formed by a tip direction of a left foot and a tip direction of a right foot; and a stride width estimation unit that estimates a stride width indicating an interval between heels of the left foot and the right foot, based on the angle.

According to a second example aspect of this example embodiment, an estimation method includes: calculating an angle formed by a tip direction of a left foot and a tip direction of a right foot; and estimating a stride width indicating an interval between heels of the left foot and the right foot, based on the angle.

According to a third example aspect of this example embodiment, an estimation program causes a computer of an estimation device to function as: an angle calculation means for calculating an angle formed by a tip direction of a left foot and a tip direction of a right foot; and a stride width estimation means for estimating a stride width indicating an interval between heels of the left foot and the right foot, based on the angle.

Effects of the Invention

According to the present invention, it is possible to more accurately estimate stride width indicating the interval between the heels of the left foot and the right foot only by the acceleration and the angular velocity measured by a sensor device provided in each sole of both feet.

EXAMPLE EMBODIMENT

Hereinbelow, a fatigue estimation device according to an example embodiment of the present invention will be described with reference to the drawings.

Figure 1:
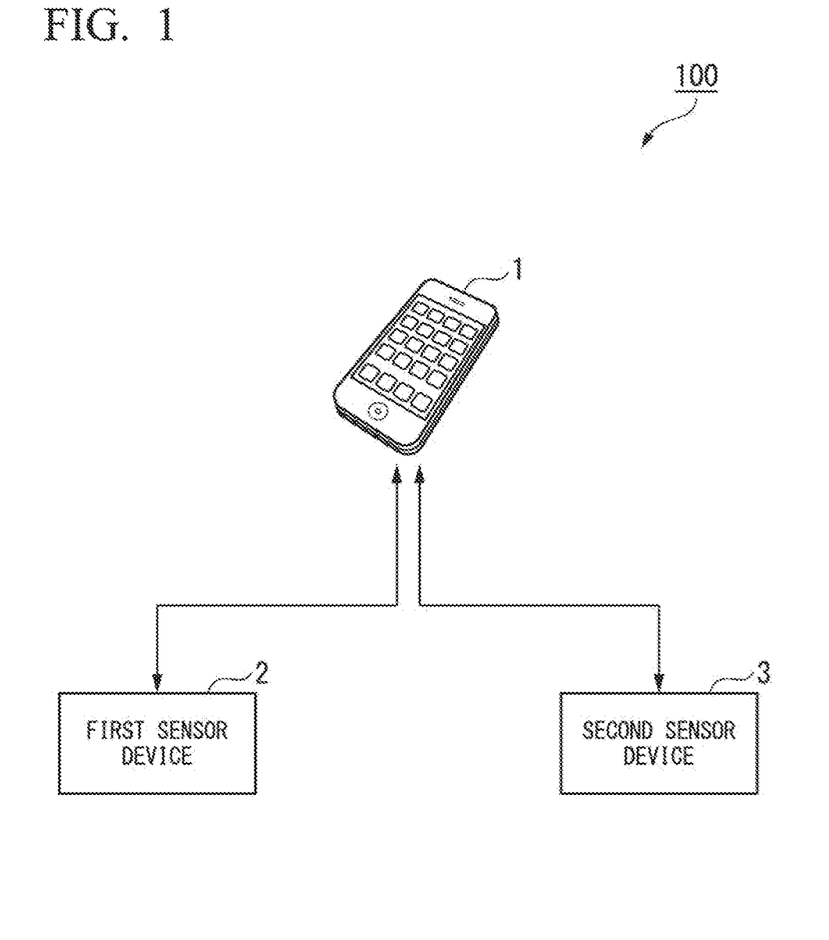
FIG. 1 is a diagram showing a schematic configuration of a fatigue estimation system according to an example embodiment of the present invention.

FIG. 1 is a diagram showing a schematic configuration of a fatigue estimation system according to the same example embodiment.

As shown in FIG. 1, the fatigue estimation system 100 is composed of at least an estimation device 1, a first sensor device 2, and a second sensor device 3. The estimation device 1 is communicatively connected with the first sensor device 2 and the second sensor device 3 in order to acquire the sensing information detected by the first sensor device 2 and the second sensor device 3.

The first sensor device 2 and the second sensor device 3 are respectively mounted to the sole of a shoe. The first sensor device 2 and the second sensor device 3 measure the acceleration and the angular velocity of the foot. As an example, the first sensor device 2 measures the left acceleration and the angular velocity, and the second sensor device 3 measures the acceleration and the angular velocity of the right foot. The estimation device 1 receives sensing information indicating acceleration and angular velocity from each of the first sensor device 2 and the second sensor device 3, and based on the sensing information, calculates a stride width D indicating the distance between the heels of the left foot and the right foot during walking.

The estimation device 1 may be a mobile terminal such as a smartphone. Moreover, the estimation device 1 may be any device provided the device receives sensing information from the first sensor device 2 and the second sensor device 3 and performs processing for estimating the user's stride width and fatigue. For example, the estimation device 1 may be a server device provided remotely.

Figure 2:
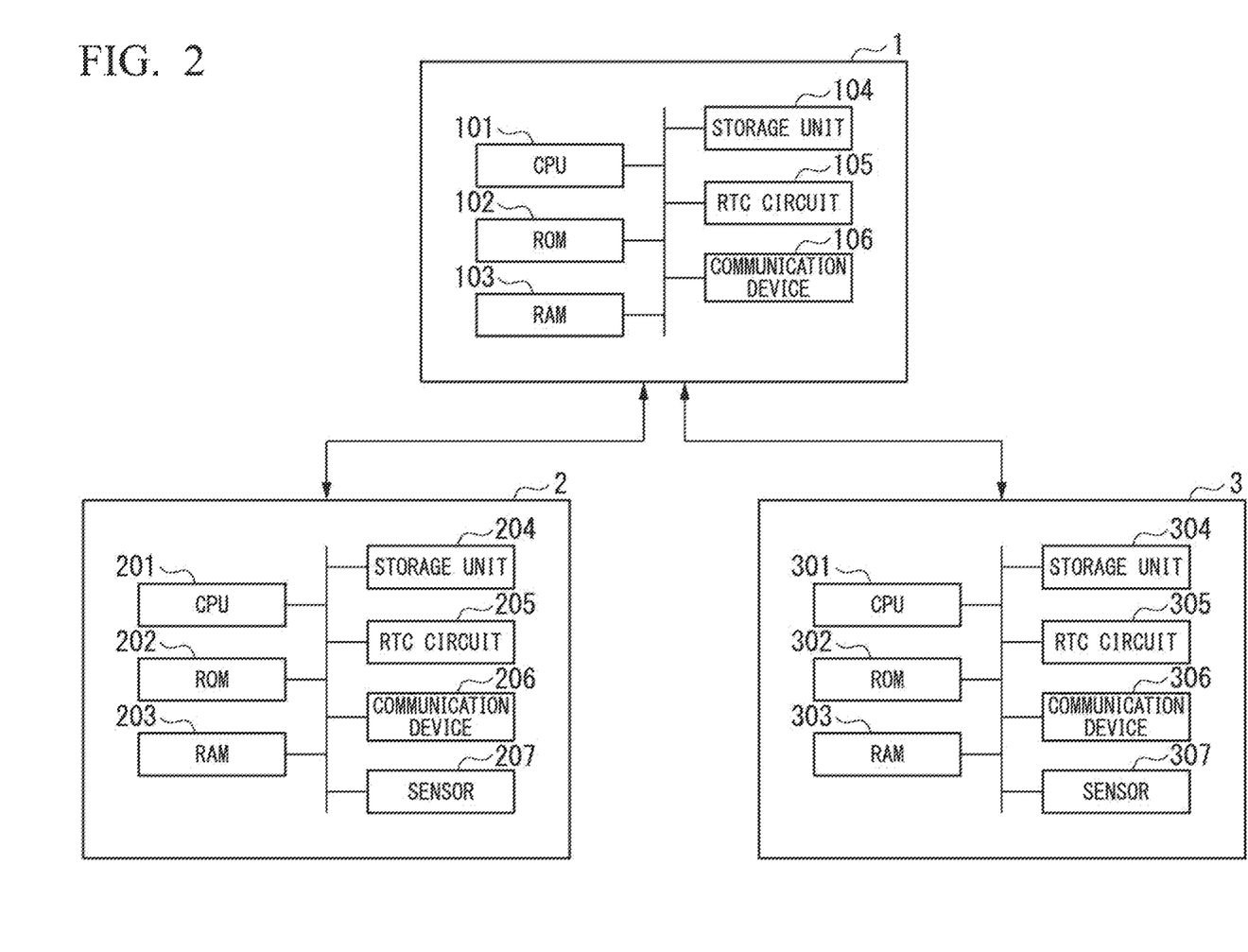
FIG. 2 is a hardware configuration diagram of an estimation device, a first sensor device, and a second sensor device according to the example embodiment of the present invention.

FIG. 2 is a hardware configuration diagram of the estimation device, the first sensor device, and the second sensor device.

The estimation device 1 is a computer including hardware such as a CPU (Central Processing Unit) 101, a ROM (Read Only Memory) 102, a RAM (Random Access Memory) 103, a storage unit 104, an RTC circuit 105, and a communication device 106.

The first sensor device 2 is a computer including hardware such as a CPU 201, a ROM 202, a RAM 203, a storage unit 204, an RTC circuit 205, a communication device 206, and a sensor 207.

The second sensor device 3 is a computer including hardware such as a CPU 301, a ROM 302, a RAM 303, a storage unit 304, an RTC circuit 305, a communication device 306, and a sensor 307.

In the present example embodiment, the sensor 207 included in the first sensor device 2 and the sensor 307 included in the second sensor device 3 are each constituted by an inertial measurement unit (IMU) that senses acceleration and angular velocity based on foot movement when the user walks.

Figure 3:
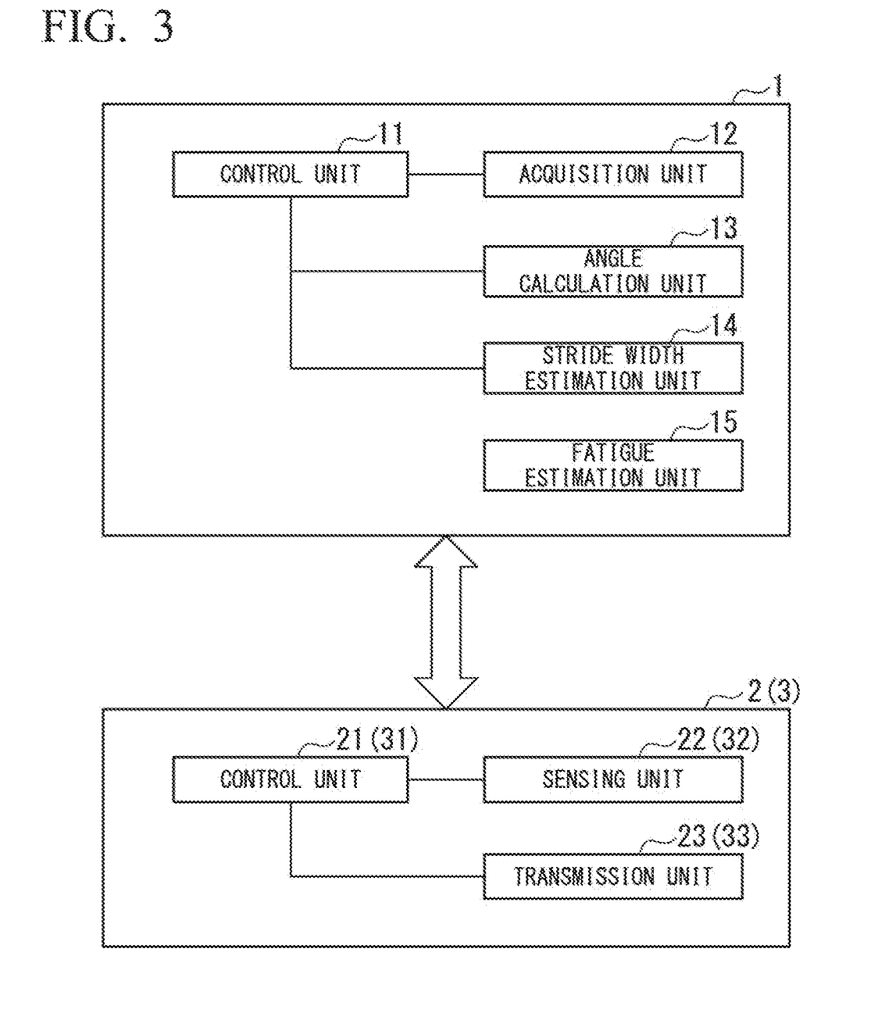
FIG. 3 is a function block diagram of an estimation device, a first sensor device, and a second sensor device according to an example embodiment of the present invention.

FIG. 3 is a function block diagram of the estimation device, the first sensor device, and the second sensor device.

The estimation device 1 executes a fatigue estimation program stored in advance. Thereby, the estimation device 1 exhibits at least the functions of a control unit 11, an acquisition unit 12, an angle calculation unit 13, a stride width estimation unit 14, and a fatigue estimation unit 15.

The control unit 11 of the estimation device 1 controls other function units of the estimation device 1.

The acquisition unit 12 of the estimation device 1 acquires the sensing information.

The angle calculation unit 13 of the estimation device 1 calculates an angle Q formed by the left foot tip direction and the right foot tip direction.

The stride width estimation unit 14 of the estimation device 1 estimates the stride width D indicating the interval between the heels of the left foot and the right foot based on the angle Q formed by the left foot tip direction and the right foot tip direction.

The fatigue estimation unit 15 of the estimation device 1 estimates the fatigue of a person based on the stride width D.

The first sensor device 2 executes a sensing program stored in advance. Thereby, the first sensor device 2 includes at least a control unit 21, a sensing unit 22, and a transmission unit 23.

The control unit 21 of the first sensor device 2 controls other function units of the first sensor device 2. The sensing unit 22 of the first sensor device 2 acquires from the sensor 207 such as the IMU or the like the acceleration and the angular velocity based on the movement of the left foot when the user walks. The transmission unit 23 of the first sensor device 2 transmits the sensing information indicating the acceleration and the angular velocity of the left foot to the estimation device 1.

The second sensor device 3 executes a sensing program stored in advance. Thereby, the second sensor device 3 includes at least a control unit 31, a sensing unit 32, and a transmission unit 33.

The control unit 31 of the second sensor device 3 controls other function units of the second sensor device 3. The sensing unit 32 of the second sensor device 3 acquires from the sensor 307 of the IMU or the like the acceleration and the angular velocity based on the movement of the right foot when the user walks. The transmission unit 33 of the second sensor device 3 transmits the sensing information indicating the acceleration and the angular velocity of the right foot to the estimation device 1.

Figure 4:
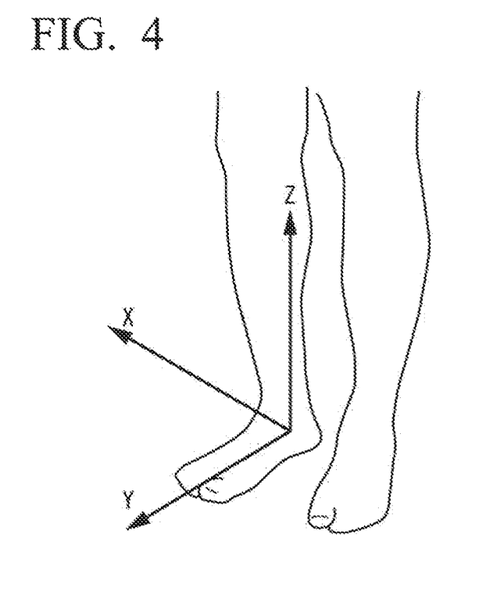
FIG. 4 is a diagram illustrating acceleration and angular velocity measured by the first sensor device and the second sensor device according to the example embodiment of the present invention.

FIG. 4 is a diagram for explaining the acceleration and the angular velocity measured by the first sensor device and the second sensor device.

In the present example embodiment, the first sensor device 2 and the second sensor device 3 detect the acceleration and angular velocity about each axis of a Z-axis along the leg axis with the heel of the foot serving as the origin, a Y-axis perpendicular to the Z-axis in the direction from the heel to the toe of the foot, and an X-axis perpendicular to the Z-axis and the Y-axis. The X-axis, Y-axis, and Z-axis are orthogonal to each other. The rotation angle around the X-axis is regarded as the pitch angle, the rotation angle around the Y-axis is regarded as the roll angle, and the rotation around the Z-axis is regarded as the yaw angle. The estimation device 1 calculates the angle formed by the left foot tip direction and the right foot tip direction on the basis of the acceleration and the angular velocity around the axis of each of these axes.

Figure 5:
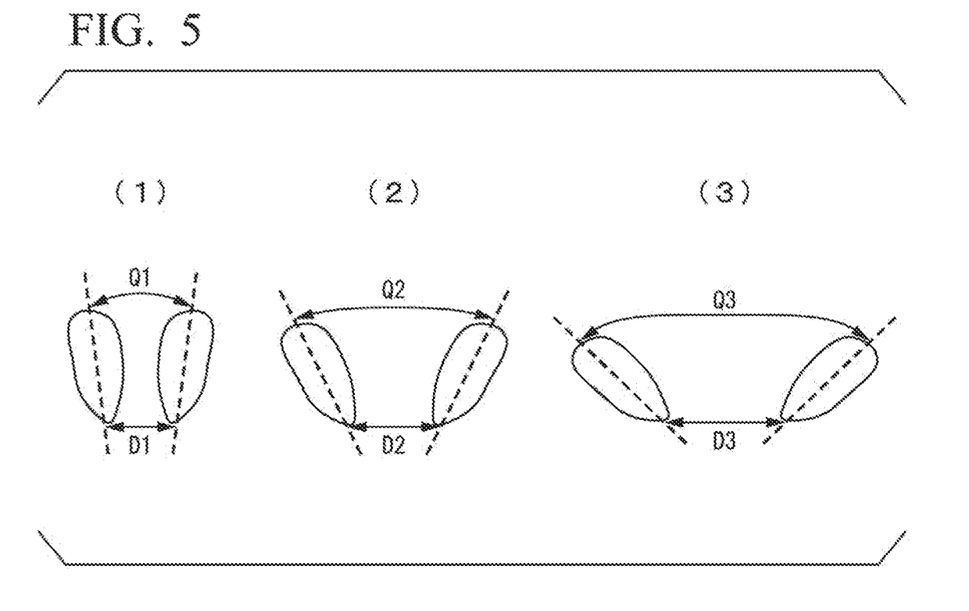
FIG. 5 is a diagram showing the relationship between the angle formed by the left foot tip direction and the right foot tip direction and the stride width during walking according to the example embodiment of the present invention.

FIG. 5 is a diagram showing the relationship between the angle formed by the left foot tip direction and the right foot tip direction and the stride width during walking.

FIG. 5(1) shows the case where the angle between the left foot tip direction and the right foot tip direction is Q1 and the stride width is D1, FIG. 5(2) shows the case where the angle between the left foot tip direction and the right foot tip direction is Q2 and the stride width is D2, and FIG. 5(3) shows the case where the angle formed by the left foot tip direction and the right foot tip direction is Q3 and the stride width is D3. In many cases, the relationship between the angle Q and the stride width D formed by the left foot tip direction and the right foot tip direction is a proportional relationship in which the larger the Q, the larger the D. In FIG. 5, the relationship between the magnitude of the angles Q and the magnitude of the stride widths D is Q1<Q2<Q3, D1<D2<D3.

Figure 6:
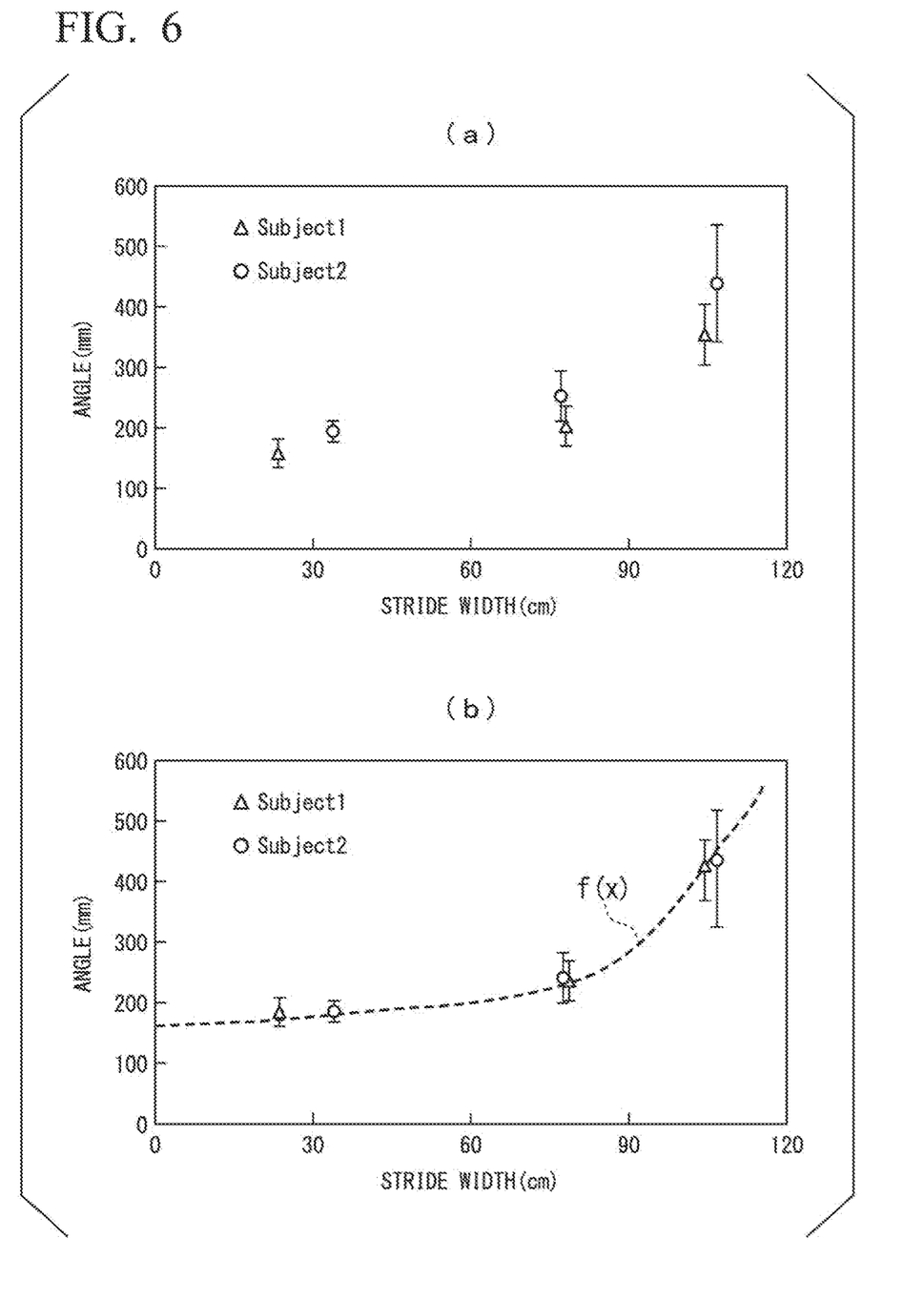
FIG. 6 is a graph showing the relationship between the angle formed by the left foot tip direction and the right foot tip direction and the stride width during walking according to an example embodiment of the present invention.

FIG. 6 is a graph showing the relationship between the angle formed by the left foot tip direction and the right foot tip direction and the stride width during walking.

Specifically, as shown in the graph of FIG. 6A, as a result of the experiment, data was obtained indicating that the larger the angle Q formed by the left foot tip direction and the right foot tip direction, the larger the stride width D. When normalized by the length L of the leg from the subject's pelvis to the sole of a foot for the purpose of creating this graph, the relationship between the angle Q formed by the left foot tip direction and the right foot tip direction and the stride width D can be expressed by the stride width calculation function f(x) as shown in FIG. 6(b). The stride width calculation function f(x) is a monotonically increasing function.

Figure 7:
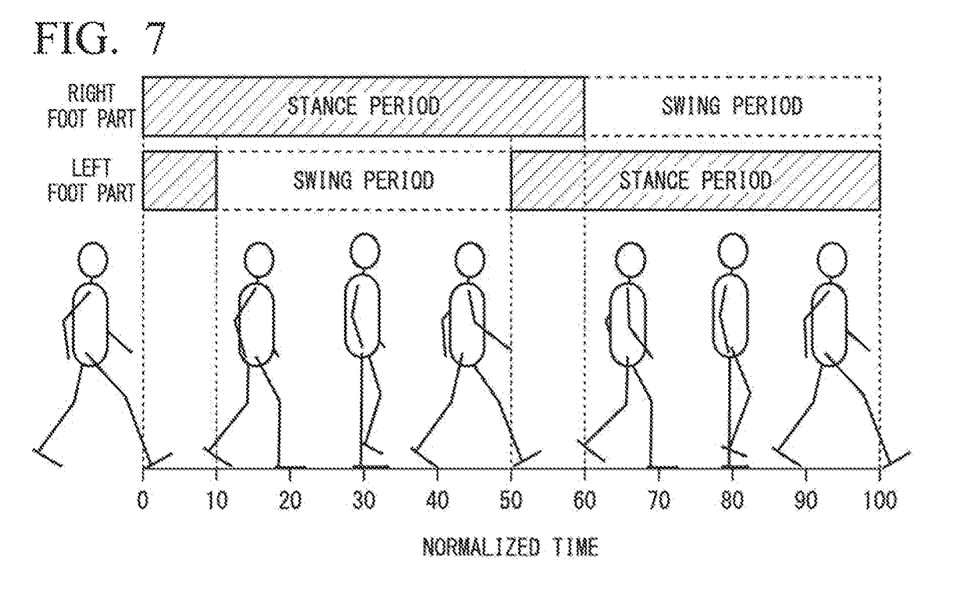
FIG. 7 is a first diagram illustrating a walking movement according to the example embodiment of the present invention.

FIG. 7 is the first diagram illustrating a walking movement.

FIG. 7 shows the stance period and the swing period of the left leg and the right leg in a person's walking movement. The stance period of the right foot represents one cycle of the movement cycle of the walking movement from 0% to 100%, with the time when the heel of one foot lands being 0%, and the time when the heel of the same foot lands next being 100%. In the movement cycle of this walking movement, the time when the heel of the right foot lands to the time when the heel takes off next is called the stance period of the right foot, and the time when the heel of the left foot lands to the time when the heel takes off next is called the stance period of the left foot. In the movement cycle of walking movement, the time when the heel of the right foot takes off to the next landing of the heel is called the swing period of the right foot, and the time when the heel of the left foot takes off to the next landing of the heel is called the swing period of the left foot.

Figure 8:
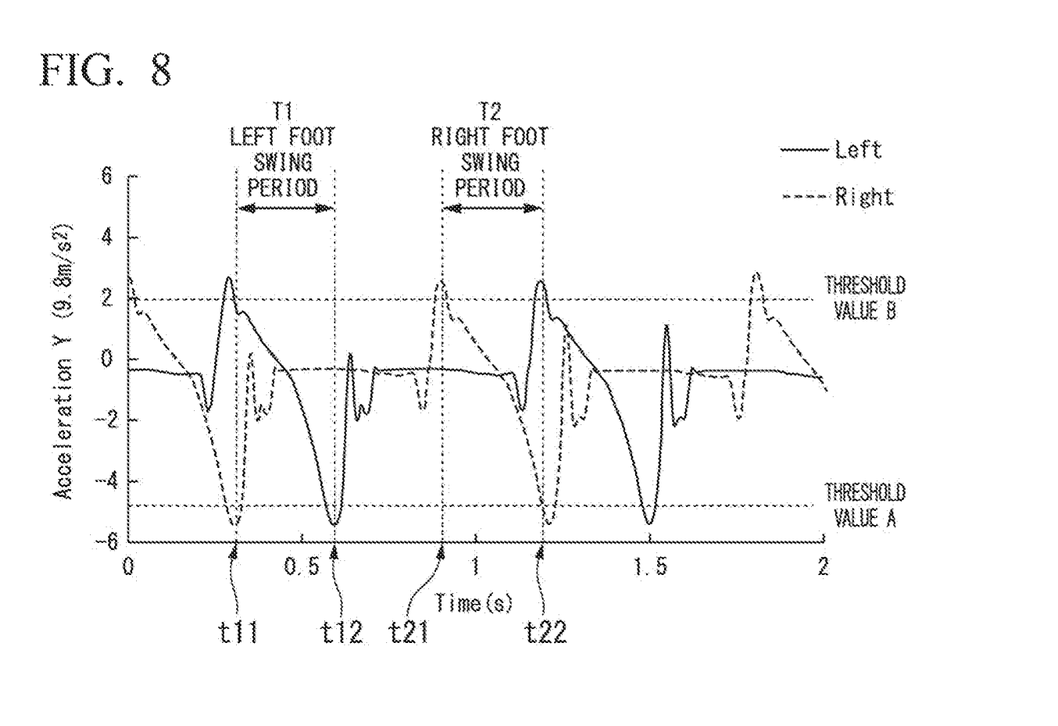
FIG. 8 is a second diagram illustrating a walking movement according to the example embodiment of the present invention.

FIG. 8 is a second diagram illustrating a walking movement.

FIG. 8 shows the vertical axis acceleration in the movement cycle of the walking movement of the left foot and the right foot, with the horizontal axis representing time and the vertical axis representing acceleration. Negative acceleration indicates downward acceleration, while positive acceleration indicates upward acceleration. Further, in FIG. 5, the solid line shows the transition of the acceleration of the left foot, and the dotted line shows the transition of the acceleration of the right foot.

Time t11 indicates the timing immediately after the left foot takes off, and time t12 indicates the timing immediately after the left foot lands. At the timing immediately after takeoff at the time t11, the upward acceleration exceeds the threshold value B and peaks, and at the timing immediately after landing at the time t12, the downward acceleration exceeds the threshold value A and peaks. In the present example embodiment, the estimation device 1 periodically detects the time t12 at which the downward acceleration exceeds the threshold value A and peaks, and detects the rotation angle around the Z axis at that time t12.

Time t21 indicates the timing immediately after the right foot takes off, and time t22 indicates the timing immediately after the right foot lands. At the timing immediately after takeoff at the time t21, the upward acceleration exceeds the threshold value B and peaks, and at the timing immediately after landing at the time t22, the downward acceleration exceeds the threshold value A and peaks. In the present example embodiment, the estimation device 1 periodically detects the time t22 at which the downward acceleration exceeds the threshold value A and peaks, and detects the rotation angle around the Z axis at that time t22.

The angle calculation unit 13 of the estimation device 1 calculates the angle Q formed by the right foot tip direction based on the rotation angle of the left foot around the Z axis at time t12 and the rotation angle of the right foot around the Z axis at time t22.

More specifically, the angle calculation unit 13 of the estimation device 1 acquires the lateral acceleration, vertical acceleration, antero-posterior acceleration of a foot, and the vertical rotational angular velocity (angular velocity around the X-axis), lateral rotational angular velocity (angular velocity around the Z axis), and inward-outward rotational angular velocity (angular velocity around the Y axis) of a foot included in the sensing information. When the back of the foot and the leg are perpendicular, there is assumed a first axis (Y axis) that connects the heel and the toe, a second axis (Z axis) that is parallel to the leg and passes through the ankle, and a third axis (X axis) that is perpendicular to the first axis and the second axis. In this case, the angular velocity of rotation around the third axis (X axis) is called the vertical rotational angular velocity of the foot. The angular velocity of rotation around the second axis (Z axis) is called the lateral rotational angular velocity of the foot. The angular velocity of rotation around the first axis (Y axis) is called the inward-outward rotational angular velocity of the foot. Then, the estimation device 1 uses an angle calculation program to calculate the vertical rotation angle of the foot indicating the angle around the third axis (X axis), the lateral rotation angle indicating the angle around the second axis (Z axis), and the inward-outward rotation angle indicating the angle around the third axis (X axis). As an angle calculation program, for example, a Madgwick filter is known, and a known technique may be used.

The angle calculation unit 13 sums the angle formed by the lateral rotation angle indicating the angle around the second axis (Z-axis) of the left foot at time t12, and the lateral rotation angle indicating the angle around the second axis (Z-axis) of the right foot at time t22, and calculates the angle Q formed by the left foot tip direction and the right foot tip direction. The angle calculation unit 13 may calculate a statistical value such as the average of the angles formed by the left foot tip direction and the right foot tip direction as the angle Q.

Figure 9:
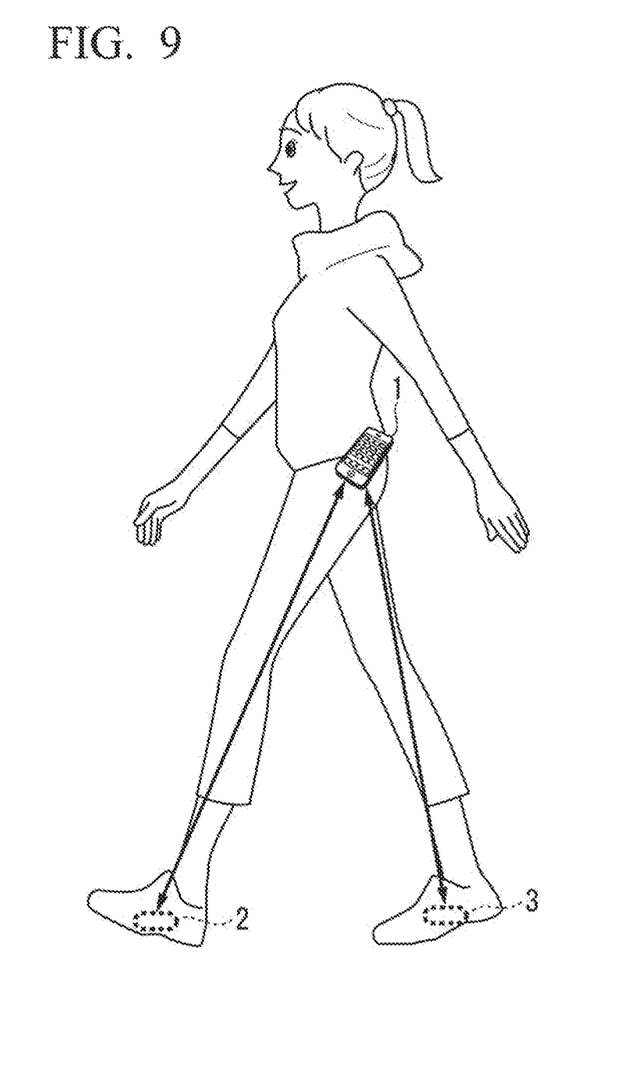
FIG. 9 is a diagram showing a usage example of an estimation device, a first sensor device, and a second sensor device according to an example embodiment of the present invention.

FIG. 9 is a diagram showing a usage example of the estimation device, the first sensor device, and the second sensor device.

As an example, the estimation device 1 is carried by the user. The first sensor device 2 is mounted in the insole of the shoe of the left foot, near the arch of the user's left foot. The second sensor device 3 is mounted in the insole of the shoe of the right foot, near the arch of the user's right foot. Then, the first sensor device 2 and the second sensor device 3 transmit the sensing information including the acceleration and the angular velocity detected according to the movement of the foot due to the walking of the user to the estimation device 1.

Figure 10:
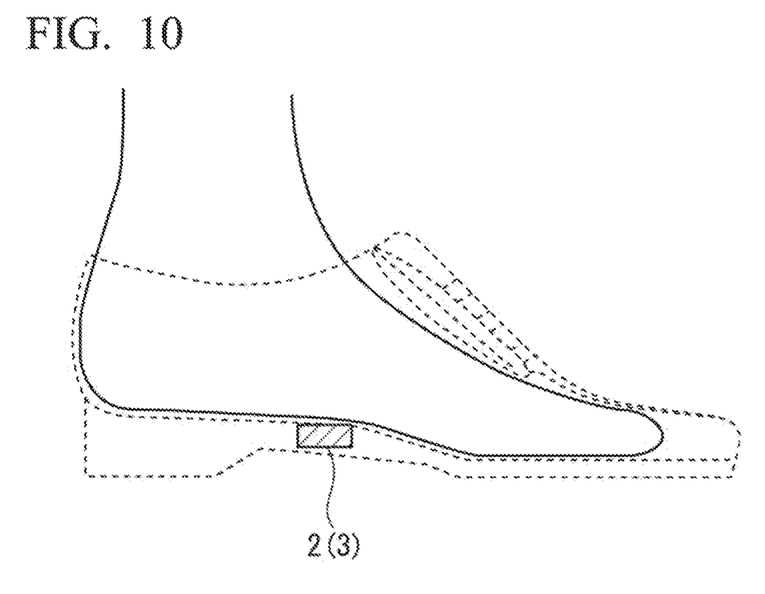
FIG. 10 is a diagram showing an outline of the sensor devices provided in a shoe sole according to the example embodiment of the present invention.

FIG. 10 is a diagram showing an outline of a sensor device provided in the sole of each shoe.

As shown in FIG. 10, the first sensor device 2 and the second sensor device 3 are provided in the soles of the shoes. The first sensor device 2 and the second sensor device 3 communicatively connect with the estimation device 1 by wireless communication.

Figure 11:
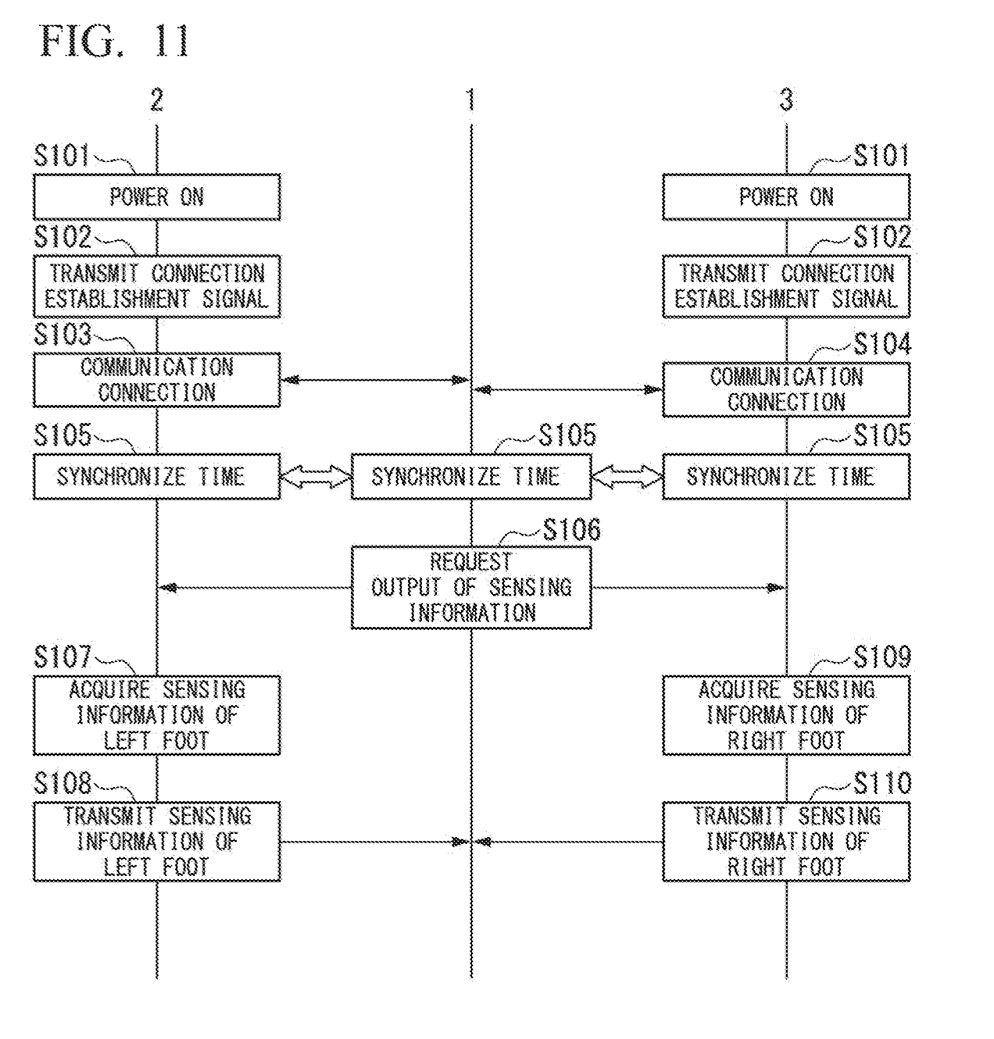
FIG. 11 is a diagram showing a processing flow of each device in the fatigue estimation system according to the example embodiment of the present invention.

FIG. 11 is a diagram showing the processing flow of each device in the fatigue estimation system.

The user aligns the shoes of both feet in parallel and turns on the power of the first sensor device 2 and the second sensor device 3 (Step S101). As a result, the communication device 206 of the first sensor device 2 and the communication device 306 of the second sensor device 3 transmit a connection establishment signal (Step S102). These communication devices 206 and 306 are for example provided with a wireless communication function such as BLE (Bluetooth Low Energy; registered trademark) and WiFi (registered trademark) to communicate with other devices.

The user operates the estimation device 1 to allow a communication connection with the first sensor device 2. As a result, the estimation device 1 and the first sensor device 2 are communicatively connected (Step S103). Similarly, the user operates the estimation device 1 to allow a communication connection with the second sensor device 3. As a result, the estimation device 1 and the second sensor device 3 are communicatively connected (Step S104). The user instructs the estimation device 1 to start processing. Then, the control unit 11 of the estimation device 1 synchronizes the time between the first sensor device 2 and the second sensor device 3 (Step S105). As a result, the times measured by the first sensor device 2, the second sensor device 3, and the estimation device 1 coincide with each other. That is, the control unit 11 of the estimation device 1 has a function of a time synchronization processing unit. The control unit 11 transmits an output request for left foot sensing information to the first sensor device 2, and transmits an output request for right foot sensing information to the second sensor device 3 (Step S106).

In the first sensor device 2, the sensing unit 22 acquires the acceleration and the angular velocity from the sensor 207 (Step S107). Then, the transmission unit 23 repeatedly transmits the sensing information of the left foot to the estimation device 1 at predetermined intervals (Step S108). The first sensor device 2 sequentially transmits the sensing information including the repeatedly detected acceleration and angular velocity to the estimation device 1. The acceleration included in the sensing information generated by the first sensor device 2 indicates acceleration in the lateral direction of the left foot, the acceleration in the vertical direction of the left foot, and the acceleration in the antero-posterior direction of the left foot. The angular velocities included in the sensing information generated by the first sensor device 2 indicate the vertical rotational angular velocity of the left foot (angular velocity around the X axis), the lateral rotational angular velocity of the left foot (angular velocity around the Z axis), and the inward-outward rotational angular velocity of the left foot (angular velocity around the Y axis).

Similarly, in the second sensor device 3, the sensing unit 32 acquires the acceleration and the angular velocity from the sensor 307 (Step S109). The transmission unit 33 repeatedly transmits the sensing information of the right foot to the estimation device 1 at predetermined intervals (Step S110). The second sensor device 3 sequentially transmits sensing information including the acceleration and angular velocity detected a plurality of times in the movement cycle of the user's walking movement to the estimation device 1. The acceleration included in the sensing information generated by the second sensor device 3 indicates the acceleration in the lateral direction of the right foot, the acceleration in the vertical direction of the right foot, and the acceleration in the antero-posterior direction of the right foot. The angular velocities included in the sensing information generated by the second sensor device 3 indicate the vertical rotational angular velocity of the right foot (angular velocity around the X axis), the lateral rotational angular velocity of the right foot (angular velocity around the Z axis), and the inward-outward rotational angular velocity of the right foot (angular velocity around the Y axis). Then, the angle calculation unit 14 of the estimation device 1 uses the angular velocity and acceleration included in the sensing information in a state in which the directions of the left and right shoes are made parallel with the toes aligned to set a reference position in which the lateral rotation angle in the state of the shoes being parallel is 0 degrees.

Specifically, the angle calculation unit 13 inputs to the angle computation program the acceleration in the lateral direction, acceleration in the vertical direction, acceleration in the antero-posterior direction, vertical rotational angular velocity (the angular velocity around the X-axis), lateral rotational angular velocity (angular velocity around the Z axis), and inward-outward rotational angular velocity (angular velocity around the Y axis) included in sensing information of the left foot that was sequentially acquired, and calculates the vertical rotation angle (angle around the X-axis), lateral rotation angle (angle around the Z axis), and inward-outward rotation angle (angle around the Y axis) of the left foot (Step S111). The angle calculation unit 13 uses the sequentially acquired sensing information and the angle calculation program to calculate the vertical rotation angle (angle around the X-axis), lateral rotation angle (angle around the Z axis), and inward-outward rotation angle (angle around the Y axis) of the right foot at a predetermined interval (Step S112). The angle calculation unit 13 stores each calculated rotation angle as a reference angle (0 degree) in which the toe directions of the left and right feet are parallel (Step S113). The user then puts on the shoes. It should be noted that the processes of steps S101 to S113 may be performed in the state of the user wearing shoes with their feet aligned.

Figure 12:
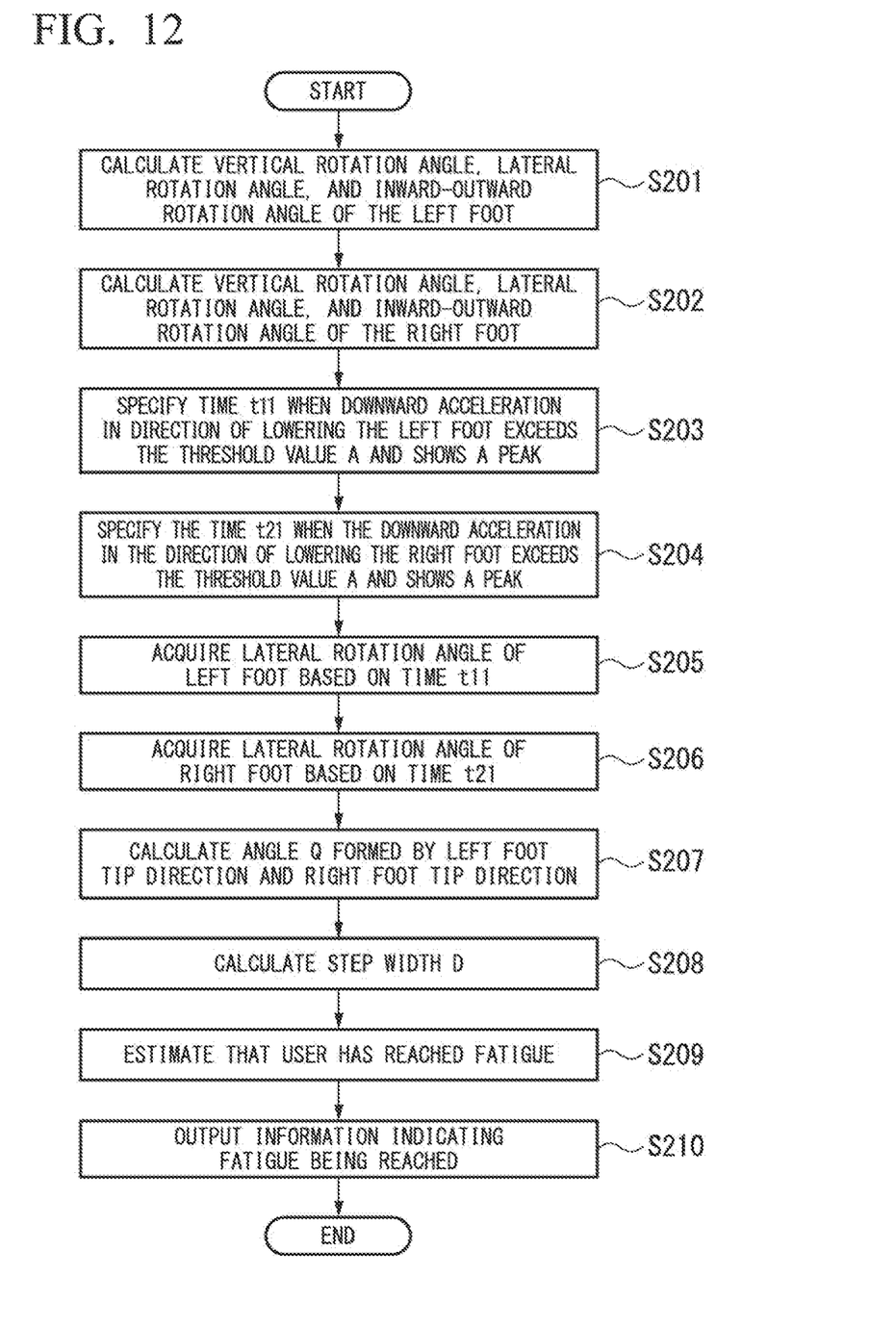
FIG. 12 is a diagram showing the processing flow of an estimation device according to the example embodiment of the present invention.

FIG. 12 is a diagram showing the processing flow of the estimation device.

Next, the processing of the estimation device 1 after the processing described with reference to FIG. 11 will be described with reference to FIG. 12.

The estimation device 1 repeatedly receives the sensing information of the left foot from the first sensor device 2 at a predetermined interval. Further, the estimation device 1 repeatedly receives the sensing information of the right foot from the second sensor device 3 at a predetermined interval. Then, the acquisition unit 12 of the estimation device 1 acquires the sensing information of the left foot and the sensing information of the right foot. The angle calculation unit 13 of the estimation device 1 sequentially acquires sensing information from the first sensor device 2 and the second sensor device 3 from the acquisition unit 12.

The angle calculation unit 13 inputs, to the angle computation program, the acceleration in the lateral direction, acceleration in the vertical direction, acceleration in the antero-posterior direction, vertical rotational angular velocity (the angular velocity around the X-axis), lateral rotational angular velocity (angular velocity around the Z axis), and inward-outward rotational angular velocity (angular velocity around the Y axis) included in sensing information of the left foot that was sequentially acquired, and calculates the vertical rotation angle (angle around the X-axis), lateral rotation angle (angle around the Z axis), and inward-outward rotation angle (angle around the Y axis) of the left foot (Step S201). These angles are rotation angles from the reference angle calculated in Step S111.

The angle calculation unit 13 uses the sequentially acquired sensing information and the angle calculation program to calculate the vertical rotation angle (angle around the X-axis), lateral rotation angle (angle around the Z axis), and inward-outward rotation angle (angle around the Y axis) of the right foot at a predetermined interval (Step S202).

The angle calculation unit 13 records the calculated information of each angle in the storage unit 104 in association with the sensing time. The sensing time may be the time counted by the first sensor device 2 or the second sensor device 3, and may be included in the sensing information.

In parallel with the aforementioned processing, the angle calculation unit 13 sequentially compares the value of the acceleration included in the sensing information of the left foot transmitted by the first sensor device 2 with the threshold value A, and specifies the time t12 when the downward acceleration (negative acceleration) in the direction of lowering the left foot exceeds the threshold value A and shows a peak (Step S203). This time is the time when the left foot lands. Similarly, the angle calculation unit 13 sequentially compares the value of the acceleration included in the sensing information of the right foot transmitted by the second sensor device 3 with the threshold value A, and specifies the time t22 when the downward acceleration (negative acceleration) in the direction of lowering the right foot exceeds the threshold value A and shows a peak (Step S204). This time is the time when the right foot lands.

The angle calculation unit 13 acquires the lateral rotation angle of the left foot recorded in the storage unit 104 in association with the time t12 or a time in the vicinity thereof (Step S205). The angle calculation unit 13 acquires the lateral rotation angle of the right foot recorded in the storage unit 104 in association with the time t12 or a time in the vicinity thereof (Step S206). With these lateral rotation angles being angles with the direction of the tip of the toe when a person is facing the front serving as a reference, the angle calculation unit 13 calculates the angle Q formed by the left foot tip direction indicated by the lateral rotation angle of the left foot and the right foot tip direction indicated by the lateral rotation angle of the right foot (Step S207). The angle calculation unit 13 calculates the angle Q formed by the left foot tip direction and the right foot tip direction at a predetermined interval.

The stride width estimation unit 14 acquires the angle Q formed by the left foot tip direction and the right foot tip direction from the angle calculation unit 13. The stride width estimation unit 14 calculates the stride width D by inputting the angle Q formed by the left foot tip direction and the right foot tip direction into the stride width calculation function f(x) (Step S208). The stride width estimation unit 14 calculates the stride width D using the angle Q and the stride width calculation function f(x) each time the angle calculation unit 13 calculates the angle Q formed by the left foot tip direction and the right foot tip direction. The stride width estimation unit 14 may calculate, for example, the average value of the stride width D calculated a plurality of times in one minute as the stride width D of a predetermined stride width calculation interval such as that one minute.

The fatigue estimation unit 15 acquires the stride width D calculated by the stride width estimation unit 14. The fatigue estimation unit 15 compares the stride width D and a fatigue threshold value. The fatigue estimation unit 15 estimates that the user has reached fatigue when the stride width D exceeds the fatigue threshold value (Step S209). If the estimation device 1 is a smartphone, the fatigue estimation unit 15 outputs information indicating that fatigue has been reached to the liquid crystal display (Step S210).

According to the above processing, the estimation device 1 can estimate the stride width D indicating the interval between the heels of the left foot and the right foot with only the acceleration and the angular velocity measured by the sensor device provided in each sole of both feet. Due to not being influenced by movements of knee joint and hip joint and the like, the estimation device 1 can estimate a more accurate value as the value of the stride width D. Further, the estimation device 1 can estimate the user's fatigue on the basis of that stride width D.

In the above processing, the estimation device 1 calculates the vertical rotation angle (angle around the X axis) of the left foot, lateral rotation angle (angle around the Z axis) of the left foot, inward-outward rotation angle (angle around the Y axis) of the left foot, and vertical rotation angle (angle around the X axis) of the right foot, lateral rotation angle (angle around the Z axis) of the right foot, and inward-outward rotation angle (angle around the Y axis) of the right foot at a predetermined interval on the basis of the sensing information. However, the first sensor device 2 and the second sensor device 3 may calculate these and transmit them to the estimation device 1, and the angle calculation unit 13 of the estimation device 1 may calculate the angle Q formed by the left foot tip direction and the right foot tip direction using the lateral rotation angle (angle around the Z axis) of the left foot at the landing timing of the left foot acquired from the first sensor device 2 and the lateral rotation angle (angle around the Z axis) of the right foot at the landing timing of the right foot acquired from the second sensor device 3.

Further, in the processing described above, the estimation device 1 estimates the time t12 when the left foot has landed on the basis of the acceleration included in the sensing information received from the first sensor device 2, and estimates the time t22 when the right foot has landed on the basis of the acceleration included in the sensing information received from the second sensor device 3. However, the first sensor device 2 may estimate the time t12 at which the left foot has landed on the basis of the acceleration measured by the device itself and transmit the time to the estimation device 1, and the second sensor device 3 may estimate the time at which the right foot has landed on the basis of the acceleration measured by the device itself and transmit the time to the estimation device 1. Then, the estimation device 1 may use the time t12 at which the left foot has landed acquired from the first sensor device 2 to specify the lateral rotation angle (angle around the Z axis) of the left foot corresponding to that time, and may use the time t22 at which the left foot has landed acquired from the second sensor device 3 to specify the lateral rotation angle (angle around the Z axis) of the right foot corresponding to that time, and may calculate the angle Q formed by the left foot tip direction and the right foot tip direction on the basis of those specified lateral rotation angles.

In the above process, the time at which feet land is estimated, and the angle Q formed between the left foot tip direction and the right foot tip direction is calculated using the lateral rotation angle at that time. However, the estimation device 1 may estimate the time of landing, specify the lateral rotation angle with the largest angle among the lateral rotation angles in the stance period measured after that time, and then use the lateral rotation angle of the left foot and right foot so specified to calculate the angle Q formed between the left foot tip direction and the right foot tip direction.

Figure 13:
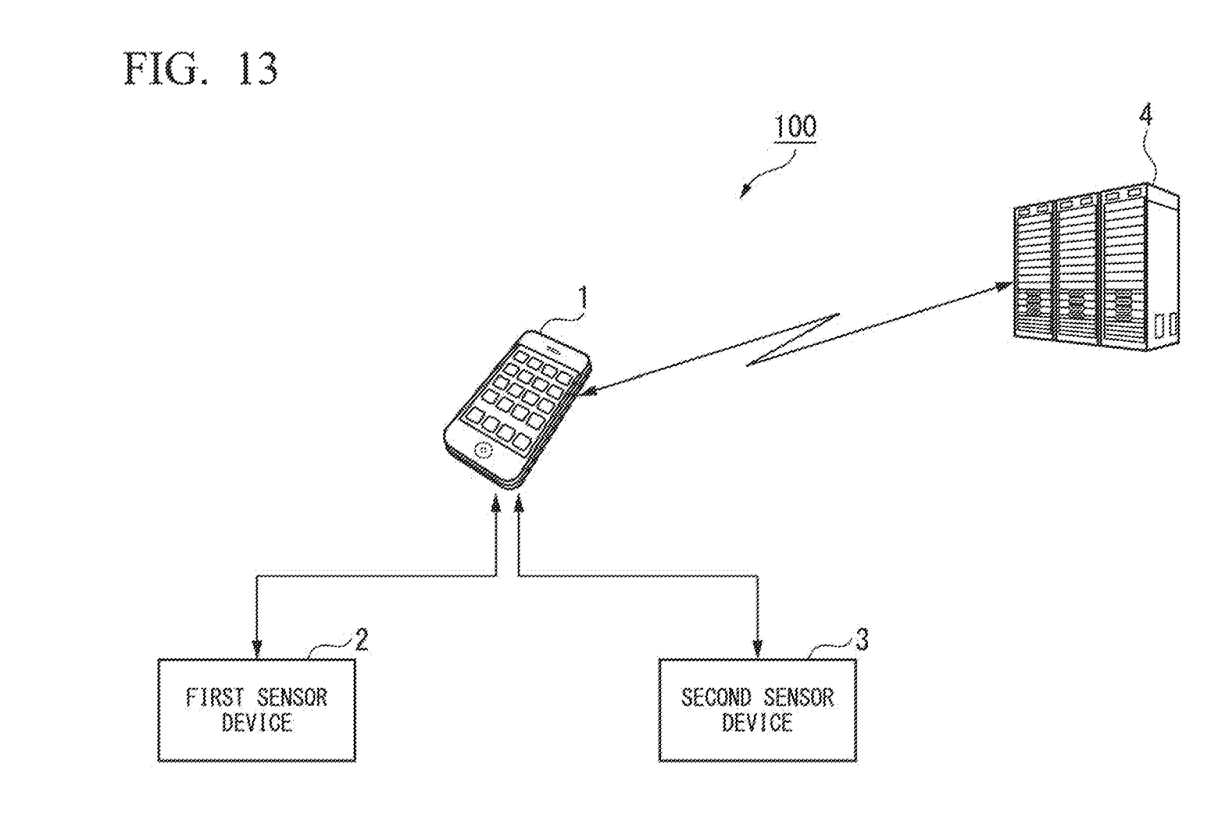
FIG. 13 is a diagram showing a schematic configuration of a fatigue estimation system according to another example embodiment of the present invention.

FIG. 12 is a diagram showing a schematic configuration of a fatigue estimation system according to another example embodiment.

The fatigue estimation system 100 may further include a server device 4, and the server device 4 may perform some of the processing of the estimation device 1 described above. That is, the server device 4 may perform any of the processing described above of the estimation device 1. In this case, the server device 4 receives the information for performing the processing via the estimation device 1, and returns the processing result to the estimation device 1. Then, the estimation device 1 may estimate the angle Q formed by the left foot tip direction and the right foot tip direction, the stride width D at that time, and the presence or absence of fatigue based on the information returned from the server device 4.

Figure 14:
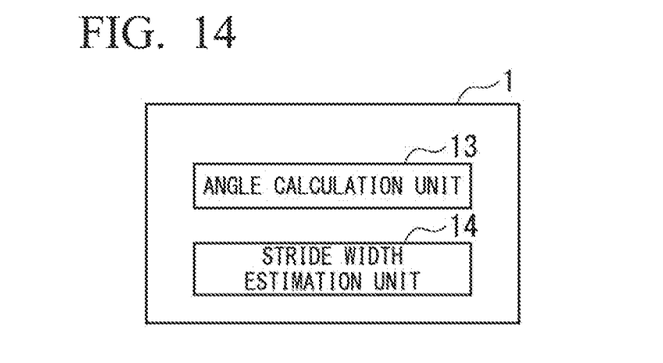
FIG. 14 is a diagram showing a minimum configuration of an estimation device according to an example embodiment of the present invention.

FIG. 13 is a diagram showing a minimum configuration of the estimation device.

Figure 15:
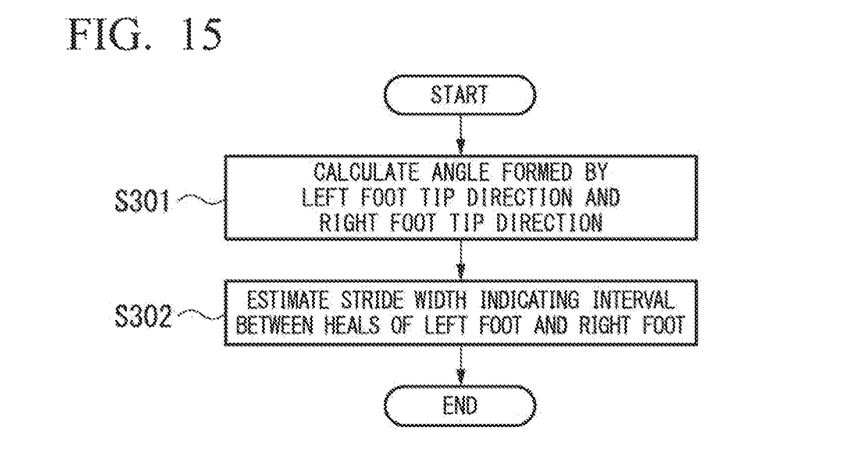
FIG. 15 is a diagram showing the processing flow of the estimation device with the minimum configuration according to the example embodiment of the present invention.

FIG. 14 is a diagram showing the processing flow of the estimation device with the minimum configuration.

The estimation device 1 includes at least an angle calculation unit and a stride width estimation unit.

The angle calculation unit 13 calculates the angle formed by the left foot tip direction and the right foot tip direction (Step S301).

The stride width estimation unit 14 estimates the stride width indicating the interval between the heels of the left foot and the right foot on the basis of the angle formed by the left foot tip direction and the right foot tip direction (Step S302).

Each of the above-mentioned devices has a computer system inside. The process of each process described above is stored in a computer-readable recording medium in the form of a program, and the process is performed by the computer reading and executing this program. Here, the computer-readable recording medium means a magnetic disk, a magneto-optical disk, a CD-ROM, a DVD-ROM, a semiconductor memory, or the like. Moreover, this computer program may be distributed to a computer through a communication line, and the computer receiving the distribution may execute the program.

The program may be for realizing some of the above-mentioned functions. Further, a so-called differential file (differential program) may be used, which can realize the above-mentioned function in combination with a program already recorded in the computer system.

DESCRIPTION OF REFERENCE SYMBOLS

1: Estimation device
2: First sensor device
3: Second sensor device
4: Server device
11, 21: Control unit
12: Acquisition unit
13: Angle calculation unit
14: Stride width estimation unit
15: Fatigue estimation unit
21, 31: Control unit
22, 32: Sensing unit
23, 33: Transmission unit

What is claimed is:

1. An estimation device comprising:
   at least one memory storing instructions; and
   at least one processor configured to execute the instructions to:
   calculate an angle formed by a tip direction of a left foot and a tip direction of a right foot;
   estimate a stride width indicating an interval between heels of the left foot and the right foot, based on the angle; and
   estimate fatigue of a person based on the stride width.

2. The estimation device according to claim 1, wherein the at least one processor is configured to execute the instructions to measure acceleration and angular velocity of the left foot and the right foot from timing at which the angle formed by the tip direction of the left foot and the tip direction of the right foot is estimated to be 0, and calculate the angle formed by the left foot tip direction and the right foot tip direction based on the acceleration and the angular velocity.

3. The estimation device according to claim 1, wherein the at least one processor is configured to execute the instructions to repeat comparison between the stride width and a threshold value to estimate the fatigue at a predetermined interval, and estimate the fatigue when the stride width has exceeded the threshold value.

4. An estimation method performed by a computer and comprising:
   calculating an angle formed by a tip direction of a left foot and a tip direction of a right foot;
   estimating a stride width indicating an interval between heels of the left foot and the right foot, based on the angle; and
   estimating fatigue of a person based on the stride width.

5. The estimation method according to claim 4, further comprising:
   measuring acceleration and angular velocity of the left foot and the right foot from timing at which the angle formed by the tip direction of the left foot and the tip direction of the right foot is estimated to be 0, and calculating the angle formed by the left foot tip direction and the right foot tip direction based on the acceleration and the angular velocity.

6. The estimation method according to claim 4, further comprising:
   repeating comparison between the stride width and a threshold value to estimate the fatigue at a predetermined interval, and estimating the fatigue when the stride width has exceeded the threshold value.

7. A non-transitory computer-readable recording medium storing an estimation program that causes a computer to execute:
   calculating an angle formed by a tip direction of a left foot and a tip direction of a right foot;
   estimating a stride width indicating an interval between heels of the left foot and the right foot, based on the angle; and
   estimating fatigue of a person based on the stride width.

* * * * *